(12) United States Patent
Carpentier et al.

(10) Patent No.: US 8,026,192 B2
(45) Date of Patent: Sep. 27, 2011

(54) FLUORINATED ALKOXY-IMINO CATALYST COMPONENTS

(75) Inventors: Jean-Francois Carpentier, Acigne (FR); Evgueni Kirillov, Rennes (FR); Christophe Thomas, Rance (FR); Abbas Razavi, Mons (BE); Nicolas Marquet, Domloup (FR)

(73) Assignee: Total Petrochemicals Research Feluy, Seneffe (Feluy) (BE)

( * ) Notice: Subject to any disclaimer, the term of this patent is extended or adjusted under 35 U.S.C. 154(b) by 43 days.

(21) Appl. No.: 12/440,871

(22) PCT Filed: Sep. 14, 2007

(86) PCT No.: PCT/EP2007/059723
§ 371 (c)(1),
(2), (4) Date: Sep. 21, 2009

(87) PCT Pub. No.: WO2008/031890
PCT Pub. Date: Mar. 20, 2008

(65) Prior Publication Data
US 2010/0029472 A1    Feb. 4, 2010

(30) Foreign Application Priority Data
Sep. 15, 2006    (EP) .................................... 06120743

(51) Int. Cl.
*B01J 31/12* (2006.01)
*C07F 7/28* (2006.01)
*C07F 7/00* (2006.01)
(52) U.S. Cl. .......................................... 502/167; 556/32
(58) Field of Classification Search ........................ None
See application file for complete search history.

(56) References Cited

FOREIGN PATENT DOCUMENTS
DE         10107045       8/2002

OTHER PUBLICATIONS
Tsukahara et al. Organometallics, 1997, 16, 3303-3313.*
Gregson et al. Dalton Transations, 2006, 3134-3140.*
Lay et al. Inorganic Chemistry, 44(20), 7226-7233, 2005.*

* cited by examiner

*Primary Examiner* — Melvin Mayes
*Assistant Examiner* — Yun Qian (57) ABSTRACT

This invention relates to fluorinated alkoxy-imino metallic complexes and their use in catalyst systems for the polymerisation or oligomerisation of ethylene and alpha-olefins.

5 Claims, 3 Drawing Sheets

FLUORINATED ALKOXY-IMINO CATALYST COMPONENTS

CROSS-REFERENCE TO RELATED APPLICATIONS

This application claims the benefit of PCT/EP2007/059723, filed Sep. 14, 2007, which claims priority from EP 06120743.7, filed Sep. 15, 2006.

The present invention discloses catalyst components based on fluorinated alkoxy-imino ligands, their method of preparation and their use in the polymerisation of olefins.

Investigations to replace ubiquitous cyclopentadienyl-type ligands in modern coordination chemistry of early transition metals have become very popular in recent years. Hard, electronegative π-donor ligands such as aryloxides/alkoxides are attractive because they offer strong metal-oxygen bonds that are expected to stabilize complexes of these electropositive metals. Also, the great variety of these ligands conveniently obtained from alcohols allows considerable stereo-electronic variations. Accordingly, group 4 metal complexes of the type $[MX_2(OZ)_2]$ and $[MX_2(OZZO)]$, where $OZ^-$ and $OZZO^{2-}$ are monoanionic and chelating dianionic ligands respectively, have retained considerable attention. Most successful developments in terms of synthetic organometallic chemistry and catalysis have appeared using aryloxide (phenolate) ligands, with significant contributions of the groups of Fujita such as for example Matsui et al. (S. Matsui, M. Mitani, J. Saito, Y. Tohi, H. Makio, N. Matsukawa, Y. Takagi, K. Tsuru, M. Nitabaru, T. Nakano, H. Tanaka, N. Kashiwa, T. Fujita, in J. Am. Chem. Soc. 2001, 123, 6847-6856) or Kojoh et al. (S. Kojoh, T. Matsugi, J. Saito, M. Mitani, T. Fujita, N. Kashiwa, Chem. Lett. 2001, 822-823) or Saito et al. (J. Saito, M. Mitani, S. Matsui, J. Y. Mohri, S. Kojoh, N. Kashiwa, T. Fujita, Angew. Chem., Int. Ed. 2001, 40, 2918-2920; Angew. Chem. 2001, 113, 3002-3004) or Mitani et al. (M. Mitani, J. Mohri, Y. Yoshida, J. Saito, S. Ishii, K. Tsuru, S. Matsui, R. Furuyama, T. Nakano, H. Tanaka, S.-I. Kojoh, T. Matsugi, N. Kashiwa, T. Fujita, J. Am. Chem. Soc. 2002, 124, 3327-3336) or Saito et al. (J. Saito, M. Mitani, J. Mohri, S. Ishii, Y. Yoshida, T. Matsugi, S. Kojoh, N. Kashiwa, T. Fujita, T. Chem. Lett. 2001, 576-577) or Mitani et al. (M. Mitani, R. Furuyama, J.-I. Mohri, J. Saito, S. Ishii, H. Terao, N. Kashiwa, T. Fujita, J. Am. Chem. Soc. 2002, 124, 7888-7889) or of the group of Coates such as for example Tian and Coates (J. Tian, G. W. Coates, Angew. Chem., Int. Ed. 2000, 39, 3626-3629; Angew. Chem. 2000, 112, 3772-3775 or Tian et al. (J. Tian, P. D. Hustad, G. W. Coates, J. Am. Chem. Soc. 2001, 123, 5134-5135) or Mason and Coates (A. F. Mason, G. W. Coates, J. Am. Chem. Soc. 2004, 126, 16326-16327).

Comparatively, group 4 metal $[MX_2(OZ)_2]$ and $[MX_2(OZZO)]$ type complexes that incorporate simple (amino-) alkoxide ligands have been much less studied. This is mainly due to aggregation problems traditionally encountered with these relatively more basic ligands (as compared to aryloxides). A valuable approach to overcome this issue consists in introducing electron-withdrawing $CF_3$ groups α to the alkoxides; this generates increased intra- and inter-molecular repulsions and a much less basic alkoxide O-atom, and in turn a much reduced bridging ability. On this principle, Jordan et al. have developed "fluorous" group 4 complexes with two pyridine-alkoxide ligands such as for example in Tsukahara et al (T. Tsukahara, D. C. Swenson, R. F. Jordan, Organometallics 1997, 16, 3303-3313). Tetradentate diamino-dialkoxide $\{ON''NO\}^{2-}$ ligands with a ethylene- (n=2), propylene- (n=3) or chiral 1,2-cyclohexyldiamine backbone flanked by two fluorinated tertiary alkoxides were recently prepared as well as neutral groups 3, 4 and 13 metal complexes derived thereof. They are described for example in Lavanant et al. (L. Lavanant, T.-Y. Chou, Y. Chi, C. W. Lehmann, L. Toupet, J.-F. Carpentier, Organometallics 2004, 23, 5450-5458) or in Amgoune et al. (A. Amgoune, L. Lavanant, C. M. Thomas, Y. Chi, R. Welter, S. Dagorne, J.-F. Carpentier, Organometallics, 2005, 24, 6279-6282) or in Kirillov et al. (E. Kirillov, L. Lavanant, C. M. Thomas, T. Roisnel, Y. Chi, J.-F. Carpentier, Chem. Eur. J. 2006, in press).

There is a demand for new catalyst systems having good activity and able to produce polymers and oligomers tailored to specific needs.

It is an aim of the present invention to prepare new catalyst components that can be used in the polymerisation or oligomerisation of olefins.

It is also an aim of the present invention to provide very active catalyst components.

It is another aim of the present invention to provide a method for polymerising or copolymerising or oligomerising olefins.

The present invention reaches, at least partially, any one of those aims.

Accordingly, the present invention discloses a new class of fluorinated alcohol-imine pro-ligand of formula wherein $R^1$ is alkyl, cycloalkyl, allyl, benzyl, or an aromatic group, all optionally substituted with one or more fluorinated alkyl group, or heteroaromatic group having at most 20 carbon atoms;

$R^2$ is hydrogen, alkyl, cycloalkyl, or aryl group having at most 20 carbon atoms, optionally substituted with one or more fluorinated alkyl groups $R^1$ and $R^2$ can be joined to form a ring;

$R^3$ and $R^4$ are each independently selected from perfluorinated alkyl groups $CF_3$, $C_nF_{2n+1}$ wherein n is an integer between 1 and 10, or from aryl or alkyl, substituted or unsubstituted, with the proviso that at least one of $R^3$ and $R^4$ is a perfluorinated alkyl group.

The perfluorinated alkyl group is acting as a strongly electron withdrawing group. This property plays two important roles:

1) it decreases the basicity of alcohol OH group and therefore inhibits the formation of aggregates around $O^-$.
2) it increases the electrophility of the metal and thus its activity in the polymerisation of olefins.

The preferred perfluorinated alkyl groups are selected from $CF_3$ or $C_nF_{2n+1}$ wherein n is an integer between 1 and 10.

Preferably, $R^1$ is phenyl, unsubstituted or substituted. The substituents, if present, can be selected from H, F, $CF_3$ or isopropyl. If the substituents are H, F or $CF_3$ they are located preferably at positions 2 and/or 3 and/or 4 and/or 5 and/or 6. If they are isopropyl, they preferably occupy positions 2 and 6.

R² can be for instance a methyl group or a phenyl group, substituted or unsubstituted.

Preferably R³ and R⁴ are the same and are $CF_3$, $C_nF_{2n+1}$, more preferably $CF_3$.

The invention also discloses a metallic complex obtained by metallation of the fluorinated alcohol-imine pro-ligand with a metal salt or a precursor of formula $MX_4$ wherein M is a metal group 4 of the Periodic Table, wherein each X is the same or different and is halogen, or alkyl or benzyl group. Preferably, X is chlorine, methyl or benzyl.

The solvent for synthesis may be selected from dichloromethane (DCM), tetrahydrofuran (THF) or a hydrocarbon and the complexation reaction is carried out at reflux.

Typically, several types of metallic complexes can be formed, depending on the relative amounts of alkoxy-imino ligand and metal unit. The preferred ratio is of two fluorinated alkoxy-imino ligands per metal unit.

The present invention further discloses an active catalyst system comprising the metallic complex and an activating agent having an ionising action.

It can be aluminoxane and comprise oligomeric linear and/or cyclic alkyl aluminoxanes represented by formula for oligomeric, linear aluminoxanes and by formula for oligomeric, cyclic aluminoxane,
wherein n is 1-40, preferably 10-20, m is 3-40, preferably 3-20 and R* is a $C_1$-$C_8$ alkyl group and preferably methyl.

The amount of activating is selected to give an Al/M ratio of from 100 to 3000, preferably of about 1000.

When X is alkyl or benzyl group, suitable boron-containing activating agents may be used. They comprise a triphenylcarbenium boronate such as tetrakis-pentafluorophenyl-borato-triphenylcarbenium as described in EP-A-0427696, or those of the general formula $[L'-H]+[BAr_1Ar_2X_3X_4]$— as described in EP-A-0277004 (page 6, line 30 to page 7, line 7). The amount of boron-containing activating agent is selected to give B/M ratio of from 0.5 to 5, preferably of about 1.

In another embodiment, according to the present invention, the metallic complex may be deposited on a conventional support impregnated with an activating agent. Preferably, the conventional support is silica impregnated with methylaluminoxane (MAO).

Alternatively, it can be an activating support such as fluorinated alumina silica.

The present invention further discloses a method for preparing an active catalyst system that comprises the steps of:
a) providing a fluorinated alcohol-imine pro-ligand;
b) complexing the pro-ligand of step a) with a metallic salt or precursor $MX_4$ in a solvent;
c) retrieving a catalyst component;
d) activating the catalyst component with an activating agent having an ionising action;
e) optionally adding a cocatalyst;
f) retrieving an active oligomerisation or polymerisation catalyst system.

Alternatively, in step d), the catalyst component is deposited on a support impregnated with an activating agent or on a fluorinated activating support.

The cocatalyst may be selected from triethylaluminium, triisobutylaluminum, tris-n-octylaluminium, tetraisobutyl-dialuminoxane or diethyl zinc.

The active catalyst system is used in the oligomerisation and in the homo- or copolymerisation of ethylene and alpha-olefins.

The present invention discloses a method for the oligomerisation or the homo- or copolymerisation of ethylene and alpha-olefins that comprises the steps of:
a) injecting the active catalyst system into the reactor;
b) injecting the monomer and optional comonomer;
c) maintaining under polymerisation conditions;
d) retrieving the oligomers and/or polymer.

The pressure in the reactor can vary from 0.5 to 50 bars, preferably from 5 to 25 bars.

The polymerisation temperature can range from 10 to 100° C., preferably from 50 to 85° C.

Preferably the monomer and optional comonomer are selected from ethylene, propylene, 1-hexene, 1-octene or styrene.

The present invention also discloses the polymers obtained with the new catalyst systems.

EXAMPLES

Synthesis of 4,4,4-trifluoro-3-hydroxy-3-(trifluoromethyl)butan-2-one (1)

The synthesis was carried out following the method described by Lay et al. (E. Lay, Y.-H. Song, Y.-C. Chiu, Y.-M. Lin, Y. Chi, A. J. Carty, S.-M. Peng, G.-H. Lee, in Inorg. Chem. 2005, vol. 44, 7226).

A stainless steel autoclave was charged with 12.5 g (75.0 mmol) of hexafluoroacetone sesquihydrate and 45 mL of acetone. The autoclave was sealed and heated at a temperature of 140° C. for from 85 to 100 h. Excess acetone and water formed were removed under reduced pressure and the residue was vacuum transferred to yield 5.71 g of (1) as a viscous colourless liquid with a yield of 34%.

Synthesis of 3,3,3-trifluoro-2-hydroxy-1-phenyl-2-(trifluoromethyl)propan-1-one (2)

A stainless steel autoclave was charged with 13.5 g (70.0 mmol) of hexafluoroacetone sesquihydrate and 7.8 mL (66.7 mmol) of acetophenone. The autoclave was sealed and heated at a temperature of 160° C. for 120 h. The reaction mixture was subjected to rotary evaporation to remove water. Then, the residue was vacuum transferred to a condenser to yield a viscous colourless liquid which rapidly crystallised at ambient temperature to give 15.5 g of 2 as an off-white crystalline solid with a yield of 86%.

The NMR spectrum was as follows: $^1$H NMR (200 MHz, CDCl$_3$, 298K): δ (ppm) 3.50 (s, 2H, CH$_2$), 7.23 (s, 1H, OH), 7.58 (t, $^3$J=7.5 Hz, 2H, m-H), 7.74 (t, $^3$J=7.5 Hz, 1H, p-H), 7.99 (d, $^3$J=7.5 Hz, 1H, o-H). $^{19}$F NMR (188 MHz, CDCl$_3$, 298K): δ (ppm) −78.4. Anal. Calcd. for C$_{10}$H$_6$F$_6$O$_2$: C, 44.13; H, 2.22. Found: C, 45.01; H, 2.48.

Synthesis of 1,1,1-trifluoro-3-[(pentafluorophenyl)imino]-2-(trifluoromethyl)butan-2-ol (3)

In a 50 mL flask, a mixture of 0.81 g (3.61 mmol) of 1 and 0.66 g (3.60 mmol) of pentafluoroaniline in 40 mL of toluene, in the presence of a catalytic amount of para-toluene sulfonic acid (PTSA) was refluxed for 12 h using a Dean-Stark receiver. The reaction mixture was evaporated in vacuum and the residue was distilled in a Kugelrohr apparatus to give 0.65 g of a colourless oily product which rapidly crystallised at room temperature with a yield of 46%.

NMR results were as follows: $^1$H NMR (200 MHz, CDCl$_3$, 298K): δ (ppm) 2.13 (s, 3H, CH$_3$), 3.09 (s, 2H, CH$_2$), 7.60 (s, 1H, OH). $^{19}$F NMR (188 MHz, CDCl$_3$, 298K): δ (ppm) −162.0 (m, 2F, m-F), −160.0 (t, $^3$J=22.0 Hz, 1F, p-F), −151.0 (d, $^3$J=22.0 Hz, 2F, o-F), −78.4 (s, 6F, CF$_3$). Anal. Calcd. for C$_{12}$H$_6$F$_{11}$NO: C, 37.04; H, 1.55. Found: C, 37.41; H, 2.04.

Figure 1:
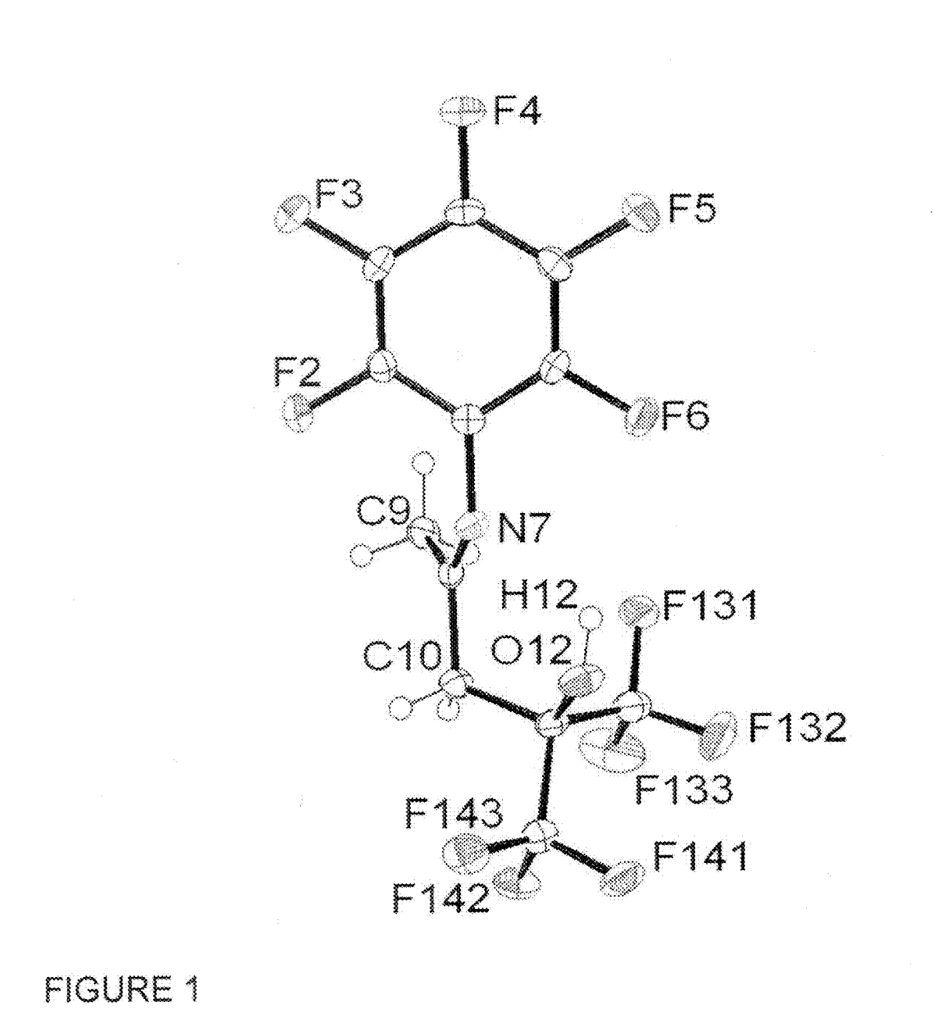
FIG. 1 represents the crystal structure of pro-ligand 3.

The crystal structure of ligand 3 is represented in FIG. 1

Synthesis of 3-[(2,6-diisopropylphenyl)imino]-1,1,1-trifluoro-2-(trifluoromethyl)butan-2-ol (4)

In a 50 mL flask, a mixture of 4.5 g (20.08 mmol) of 1 and 3.8 mL (20.15 mmol) of 2,6-diisopropylaniline in 40 mL of toluene, in the presence of a catalytic amount of PTSA, was refluxed for 15 h using a Dean-Stark receiver. The reaction mixture was evaporated in vacuum and the residue was distilled in a Kugelrohr apparatus to give 0.74 g of 4 as a pale-yellow oily product with a yield of 10%.

The NMR results were as follows: $^1$H NMR (200 MHz, CDCl$_3$, 298K): δ (ppm) 1.15 (d, 6H, iPr), 1.19 (d, 6H, iPr), 1.86 (s, 3H, CH$_3$), 2.69 (m, 2H, iPr), 2.97 (s, 2H, CH$_2$), 7.18 (m, 3H, arom.), 9.68 (s, 1H, OH). $^{19}$F NMR (188 MHz, CDCl$_3$, 298K): δ (ppm) −79.1. Anal. Calcd. for C$_{18}$H$_{23}$F$_6$NO: C, 56.39; H, 6.05. Found: C, 56.43; H, 5.84.

Synthesis of 1,1,1-trifluoro-3-[(pentafluorophenyl)imino]-2-(trifluoromethyl)butan-2-ol (5)

In a 50 mL flask, a mixture of 2.10 g (9.37 mmol) of 1 and 1.0 mL (10.97 mmol) of aniline in 40 mL of toluene, in the presence of a catalytic amount of PTSA, was refluxed for 12 h using a Dean-Stark receiver. The reaction mixture was evaporated in vacuum and the residue was distilled in a Kugelrohr apparatus to give 1.35 g of 5 as a colorless oily product which rapidly crystallised at room temperature with a yield of 48%.

The NMR results were as follows:

$^1$H NMR (200 MHz, CDCl$_3$, 298K): δ (ppm) 2.00 (s, 3H, CH$_3$), 2.94 (s, 2H, CH$_2$), 6.79 (d, $^3$J=7.3 Hz, 2H, o-H), 7.23 (t, $^3$J=7.3 Hz, 1H, p-H), 7.39 (t, $^3$J=7.3 Hz, 3H, m-H), 9.04 (s, 1H, OH). $^{19}$F NMR (188 MHz, CDCl$_3$, 298K): δ (ppm) −78.3. Anal. Calcd. for C$_{12}$H$_{11}$F$_6$NO: C, 48.17; H, 3.71. Found: C, 48.10; H, 3.56.

Reaction of 3 and Zr(CH$_2$Ph)$_4$. Synthesis of [OC(CF$_3$)$_2$CH$_2$C(CH$_3$)=N(C$_6$F$_5$)]$_2$Zr(CH$_2$Ph)$_2$ (6) and [OC(CF$_3$)$_2$CH$_2$C(CH$_3$)=N(C$_6$F$_5$)]$_2$Zr[OC(CF$_3$)$_2$CH=C(CH$_3$)N(C$_6$F$_5$)] (7)

A Teflon-valved NMR tube was charged with 68.3 mg (175.5 μmol) of 3 40.0 mg (87.8 μmol) of and Zr(CH$_2$Ph)$_4$ and about 0.5 mL of dry toluene-d$_8$ under vacuum. The tube was kept for a period of time of 3 to 4 h at a temperature of −30° C. and afterwards NMR spectroscopy was recorded. The formation of complex 6 proceeded with a yield of about 80% according to $^1$H NMR. Green-yellow crystals of 6 suitable for X-ray were obtained by cooling the solution at a temperature of −30° C. for a period of time of 20 h.

The NMR results for 6 were as follows:

$^1$H NMR (500 MHz, toluene-d$_8$, 298K): δ (ppm) 1.23 (s, 6H, CH$_3$), 2.42 (s, 4H, ZrCH$_2$Ph), 2.78 (s, 4H, OC(CF$_3$)$_2$CH$_2$), 6.9-7.2 (m, 10H, Ph). $^{19}$F NMR (188 MHz, toluene-d$_8$, 298K): δ (ppm) −167.0 (m, 4F, m-F), −163.0 (t, 2F, p-F), −167.0 (br s, 4F, o-F), −82.0 (s, 12F, CF$_3$).

Due to the instability of 6 at room temperature in toluene solution, $^{13}$C NMR and HETCOR spectra were not recorded.

The toluene solution of complex 6 was kept in the glovebox at room temperature for one day, after which time period 36.3 mg (28.9 μmol) of pale-yellow crystals of (7) grew and were recovered with a yield of 33%.

The NMR results for 7 were as follows:

$^1$H NMR (500 MHz, benzene-d$_6$, 298K): δ (ppm) 1.14 (s, 3H, CH$_3$), 1.16 (s, 6H, CH$_3$), 3.28 (s, 4H, OC(CF$_3$)$_2$CH$_2$), 4.93 (s, 1H, N(CH$_3$)CH=C(CF$_3$)$_2$). $^{13}$C{$^1$H} NMR (125 MHz, benzene-d$_6$, 298 K): δ (ppm) 22.3 (CH=C(CH$_3$)N), 26.0 (CH$_2$C(CH$_3$)=N), 39.8 (CH$_2$C(CH$_3$)=N), 81.3 (CF$_3$)$_2$CCH=C(CH$_3$)N, 99.3 (CH=C(CH$_3$)N), 150.0 (CH=C(CH$_3$)N), 193.3 (CH$_2$C(CH$_3$)=N), the remaining resonances were not observed by HMQC and HMBC methods.

$^{19}$F NMR (188 MHz, benzene-d$_6$, 298K): δ (ppm) −164.9 (m, 2F), −161.6 (m, 4F), −155.9 (m, 2F), −149.7-147.3 (br m, 7F), −82.6 (s, 6F, CF$_3$), −82.2 (s, 12F, CF$_3$). Anal. Calcd. for C$_{36}$H$_{14}$F$_{33}$N$_3$O$_3$Zr: C, 34.46; H, 1.12. Found: C, 35.10; H, 1.50.

Figure 2:
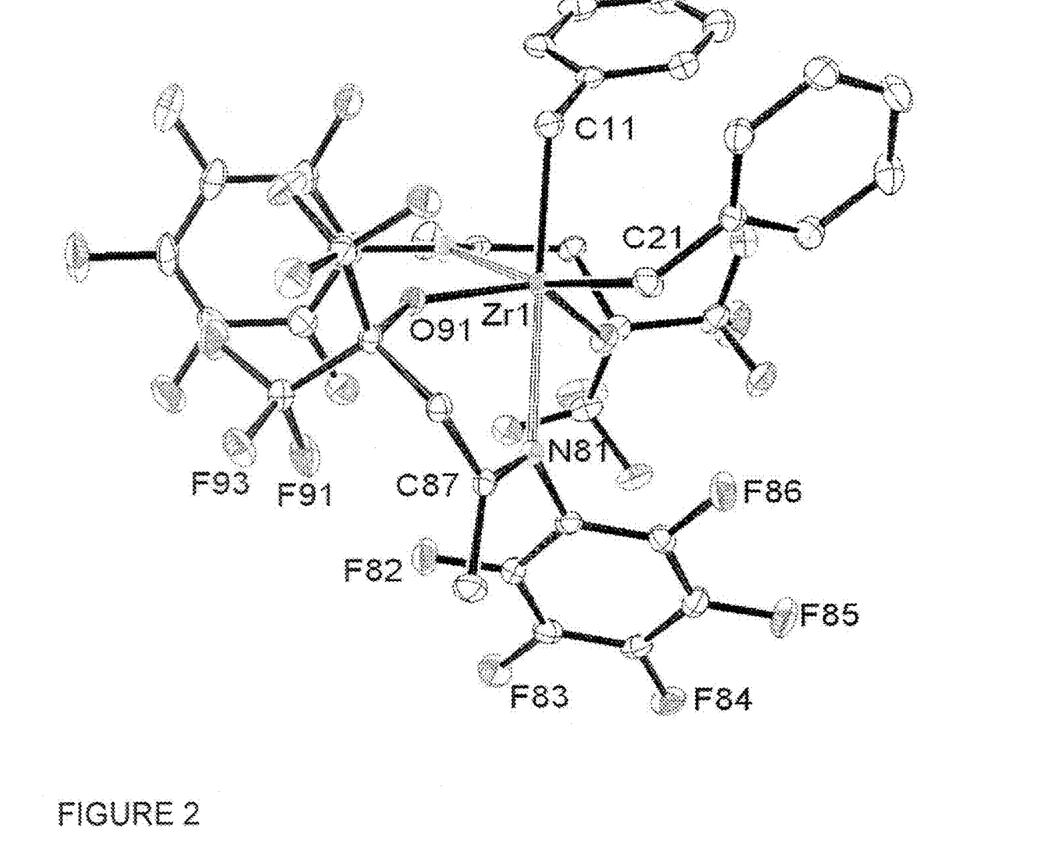
FIG. 2 represents the crystal structure of complex 6.
Figure 3:
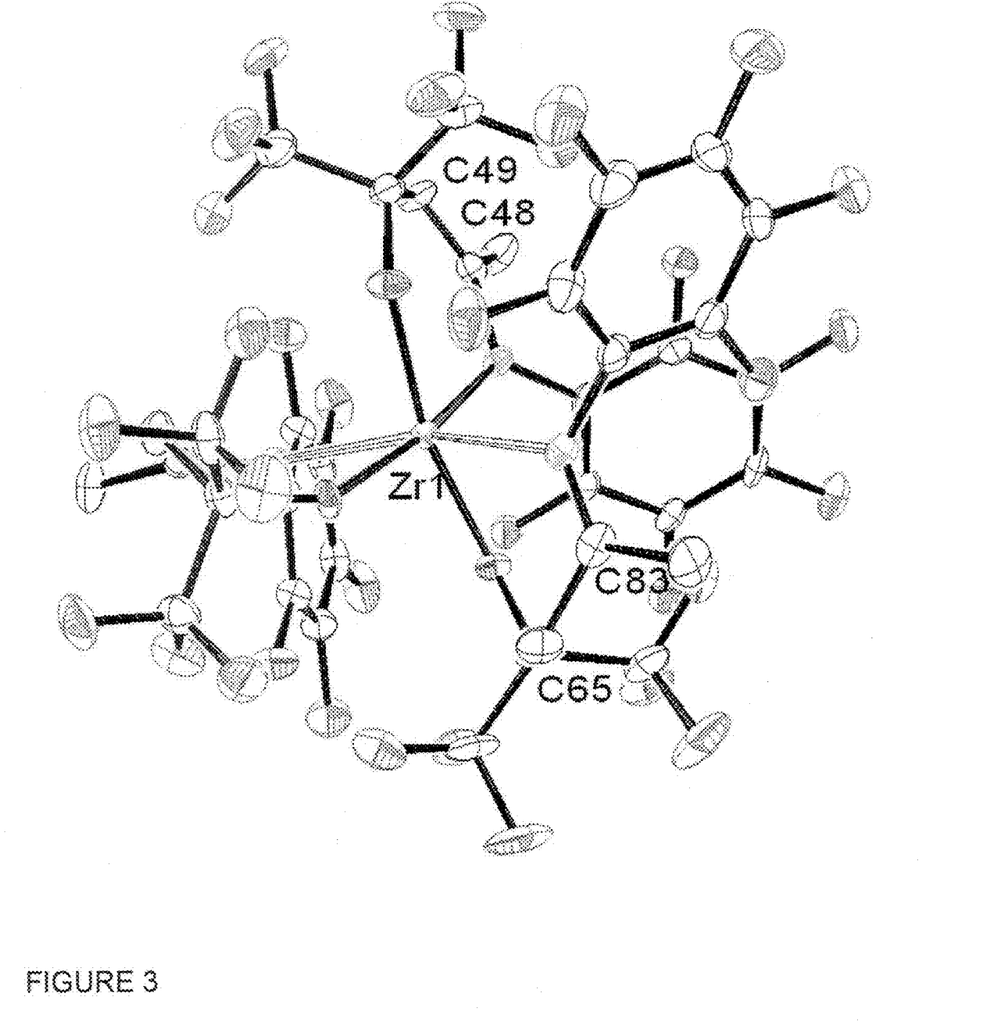
FIG. 3 represents the crystal structure of complex 7.

The crystal structure of complex 6 is represented in FIG. 2 and the crystal structure of complex 7 is represented in FIG. 3.

Synthesis of [OC(CF$_3$)$_2$CH$_2$C(CH$_3$)=N(C$_6$F$_5$)]$_2$ZrCl$_2$ (8)

To a solution of 0.70 g (1.79 mmol) of 3 in 30 mL of Et$_2$O kept at a temperature of −78° C. were added dropwise 0.72 mL of a 2.5M solution in hexanes (1.79 mmol) of n-butyllithium. The reaction mixture was stirred for a period of time of 3 h at a temperature of −78° C. and then allowed to warm up to room temperature over 1 h. Volatiles were removed under vacuum and 0.21 g (0.90 mmol) of solid ZrCl$_4$ were added in the glovebox. 30 mL of fresh Et$_2$O were vacuum transferred to the reaction mixture and the latter was stirred for a period of time of 12 h at room temperature. Volatiles were removed in vacuum, and 30 mL of dichloromethane were vacuum transferred onto the residue. The resulting solution was filtered off, the pale-pink solution was concentrated to about 5-7 mL and 5 mL of hexane were added. After a period of time of 10 h at a temperature of −30° C., a pink microcrystalline solid precipitated out. It was separated and dried under vacuum to give 0.10 g of 8 as a white solid with a yield of 12%.

NMR results for 8 were as follows:

$^1$H NMR (200 MHz, CD$_2$Cl$_2$, 298K): δ (ppm) 2.12 (s, 6H, CH$_3$), 3.12 (s, 4H, CH$_2$).

$^{19}$F NMR (188 MHz, CD$_2$Cl$_2$, 298K): δ (ppm) −163.2 (m, 4F, m-F), −160.7 (t, $^3$J=25.6 Hz, 2F, p-F), −151.4 (d, $^3$J=25.6 Hz, 4F, o-F), −78.4 (s, 12F, CF$_3$).

Due to the poor solubility of 8, $^{13}$C and HETCOR NMR were not recorded.

Anal. Calcd. for C$_{24}$H$_{10}$Cl$_2$F$_{22}$N$_2$O$_2$Zr: C, 30.72; H, 1.07. Found: C, 30.50; H, 1.01.

Polymerisation of Ethylene.

All polymerisations were carried out in 50 mL of toluene, at a temperature of 50° C. and for a period of time of 30 minutes. The polymerisation conditions and results are summarised in Tables I and II.

TABLE I

| Catalyst | Amount | Activator (eq.) | Ethylene Pressure (atm) | Activity (kg·mol⁻¹·h⁻¹) | $T_m$ (°C) | Oligomers formed? |
|---|---|---|---|---|---|---|
|  | 11.5 mg 13.03 μmol | MAO 1190 eq. | 8 | 44 | 133 | n.d. |
| " | 10.9 mg 12.35 μmol | MAO 1256 eq. | 6.5 | 46 | | possible |
| " | 11 mg 12.5 μmol | TIBAL: 40 eq. BF$_{20}$Tityl: 3 eq. | 8 | 1.4 | | n.d. |
|  | 11 mg 14.5 μmol | MAO 1355 eq. | 8 | 53 | 140 | n.d. |
|  | 10.5 mg 11.8 μmol | MAO 1446 eq. | 8 | 58 | 136 | n.d. |
|  | 10 mg 13.1 μmol | MAO 1500 eq. | 8 | 65 | 135 | n.d. |
| " | 10.6 mg 13.9 μmol | MAO 1116 eq. | 6.5 | 33 | | possible |

TABLE II

| Catalyst | Amount | Activator (eq.) | Ethylene Pressure (atm) | Activity (kg·mol⁻¹·h⁻¹) | $T_m$ (°C) | Oligomers formed? |
|---|---|---|---|---|---|---|
|  | 10.5 mg 12.5 μmol | MAO 1240 eq. | 6.5 | 74 | 136 | no oligomer |
|  | 10.1 mg 14.1 μmol | MAO 1098 eq. | 6.5 | 67 | 137 | no oligomer |

TABLE II-continued

| Catalyst | Amount | Activator (eq.) | Ethylene Pressure (atm) | Activity (kg·mol⁻¹·h⁻¹) | $T_m$ (°C.) | Oligomers formed? |
|---|---|---|---|---|---|---|
|  | 12 mg 12.5 μmol | TIBAL: 48 eq. BF₂₀Trityl: 2.2 eq. | 6.5 | no polymer | — | possible |
|  | 12 mg. | TIBAL: BF₂₀Trityl: | 5 | 10 | 144 | n.d. |
| "* | 12 mg | MAO 500 eq. | 1 | 7 | 141 | n.d. |

25

Polymerisation of Styrene.

All polymerisations were carried out in 50 mL of toluene, at room temperature (about 25° C.) and for a period of time of 2 hours. The polymerisation conditions and results are summarised in Table III.

TABLE III

| Catalyst | Amount | Styrene (eq.) | MAO (eq.) | Activity (kg·mol⁻¹·h⁻¹) | Conversion | Tacticity |
|---|---|---|---|---|---|---|
|  | 10 mg 11.3 μmol | 1006 | 298 | 11.6 | 22% | atactic |
| " | 10 mg 11.3 μmol | 1006 | 1009 | 12.0 | 23% | atactic |
|  | 12 mg 16.8 μmol | 832 | 832 | 10.5 | 24% | atactic |

The invention claimed is:

1. A metallic complex formed by a process comprising: reacting via a metallation reaction, a metal salt or precursor of formula MX₄, wherein M is a metal group 4 of the Periodic Table, and wherein each X is the same or different and is a halogen, an alkyl or a benzyl group with a fluorinated alcohol-imine pro-ligand of general formula:

wherein $R^1$ is a substituted phenyl group with H, F, $CF_3$ at positions 2, 3, 4, 5, and 6, or with isopropyl at positions 2 and 6, $R^2$ is hydrogen, $C_1$ to $C_{20}$ alkyl, $C_1$ to $C_{20}$ cycloalkyl or $C_1$ to $C_{20}$ aryl group, optionally substituted with one or more fluorinated alkyl groups, $R_3$ and $R_4$ are each independently selected from perfluorinated alkyl groups, aryl or alkyl group, with the proviso that at least one of $R^3$ and $R^4$ is a perfluorinated alkyl group.

2. The metallic complex of claim 1, wherein the perfluorinated alkyl group is selected from $CF_3$ or $C_nF_{2n+1}$, wherein n is an integer between 1 and 10.

3. The metallic complex of claim 2, wherein $R^3$ and $R^4$ are the same and are $CF_3$.

4. The metallic complex of claim 1, wherein X is chlorine, methyl or benzyl.

5. The metallic complex of claim 1, wherein M is Zr or Ti.

* * * * *